US012644190B2

(12) United States Patent
Co et al.

(10) Patent No.: US 12,644,190 B2

(45) Date of Patent: Jun. 2, 2026

(54) MATERIALS AND METHODS FOR THE ELECTROCHEMICAL REDUCTION OF CARBON DIOXIDE

(71) Applicant: OHIO STATE INNOVATION FOUNDATION, Columbus, OH (US)

(72) Inventors: Anne Co, Columbus, OH (US); Joshua Billy, Newark, DE (US); Eric Coleman, Hillsboro, OR (US); Kendahl Walz, Columbus, OH (US)

(73) Assignee: Ohio State Innovation Foundation, Columbus, OH (US)

( * ) Notice: Subject to any disclaimer, the term of this patent is extended or adjusted under 35 U.S.C. 154(b) by 0 days.

(21) Appl. No.: 18/164,921

(22) Filed: Feb. 6, 2023

(65) Prior Publication Data

US 2024/0026551 A1 Jan. 25, 2024

Related U.S. Application Data

(63) Continuation of application No. 16/736,014, filed on Jan. 7, 2020, now abandoned, which is a continuation (Continued)

(51) Int. Cl.

*C25B 3/03* (2021.01)
*C25B 3/07* (2021.01)

(Continued)

(52) U.S. Cl.

CPC ................ *C25B 3/25* (2021.01); *C25B 11/04* (2013.01); *C25B 11/081* (2021.01); *G06Q 10/10* (2013.01);

(Continued)

(58) Field of Classification Search

CPC ................ C25B 3/26; C25B 3/03; C25B 3/07

(Continued)

(56) References Cited

U.S. PATENT DOCUMENTS

| | | | |
|---|---|---|---|
| 4,959,131 A | 9/1990 | Cook | |
| 9,359,681 B1 * | 6/2016 | Serov | C22C 1/08 |

(Continued)

FOREIGN PATENT DOCUMENTS

| | | | |
|---|---|---|---|
| JP | 2012112001 A * | 6/2012 | C25B 9/00 |
| WO | 2009025635 A1 | 2/2009 | |

(Continued)

OTHER PUBLICATIONS

Canter, "Use of Copper Nanofoams to Electrochemically Reduce Carbon Dioxide," Tribology & Lubrication Technology (Nov. 1, 2014 ), vol. 70, No. 11, pp. 1-3. (Year: 2014).*

(Continued)

*Primary Examiner* — Edna Wong

(74) *Attorney, Agent, or Firm* — Meunier Carlin & Curfman LLC

(57) ABSTRACT

Disclosed are methods for electrochemically reducing carbon dioxide to provide a product. The methods can comprise contacting the carbon dioxide with an electroreduction catalyst in an electrochemical cell, and applying a potential to the electrochemical cell to form the product. The electroreduction catalyst can comprise a nanoporous Cu catalyst, a nanoporous Cu-M catalyst, or a combination thereof, where M is a metal chosen from Pt, Ir, Pd, Ag, Au, Rh, Ru, Zn, Sn, Ni, Fe, Re, Ga, In, Cd, Tl, and Ti. The product can comprise a $C_2$-$C_3$ alkane, a $C_2$-$C_3$ alkene, a $C_2$-$C_3$ alcohol, a $C_2$-$C_3$ carboxylic acid, a $C_2$-$C_3$ aldehyde, or a combination thereof.

18 Claims, 5 Drawing Sheets

Related U.S. Application Data of application No. 15/516,495, filed as application No. PCT/US2015/053532 on Oct. 1, 2015, now abandoned.

(60) Provisional application No. 62/058,121, filed on Oct. 1, 2014.

(51) Int. Cl.

| | |
|---|---|
| ***C25B 3/25*** | (2021.01) |
| ***C25B 3/26*** | (2021.01) |
| ***C25B 11/04*** | (2021.01) |
| ***C25B 11/081*** | (2021.01) |
| ***G06Q 10/10*** | (2023.01) |
| ***G16H 10/60*** | (2018.01) |
| ***G16H 40/20*** | (2018.01) |
| ***G16H 50/30*** | (2018.01) |

(52) U.S. Cl.

CPC ............. *G16H 10/60* (2018.01); *G16H 40/20* (2018.01); *G16H 50/30* (2018.01); *B01D 2257/504* (2013.01); *Y02A 90/10* (2018.01)

(58) Field of Classification Search

USPC ......................... 205/413, 462, 440, 448, 450

See application file for complete search history.

(56) References Cited

U.S. PATENT DOCUMENTS

| | | | | |
|---|---|---|---|---|
| 2011/0035995 | A1 | 2/2011 | Busch | |
| 2012/0029250 | A1 | 2/2012 | Hallen et al. | |
| 2013/0048506 | A1 | 2/2013 | Chen | |
| 2013/0105304 | A1 | 5/2013 | Kaczur et al. | |
| 2013/0256123 | A1 | 10/2013 | Rahman et al. | |
| 2014/0027303 | A1 | 1/2014 | Cole | |
| 2014/0083871 | A1* | 3/2014 | Daniels .............. | G01N 27/3277 977/734 |
| 2014/0151240 | A1* | 6/2014 | Bedell ................ | B01D 53/1475 205/462 |
| 2016/0215404 | A1 | 7/2016 | Palmore | |

FOREIGN PATENT DOCUMENTS

| | | | | |
|---|---|---|---|---|
| WO | WO-2012082717 A2 * | 6/2012 | ............... | C25C 1/12 |
| WO | 2012125053 A2 | 9/2012 | | |
| WO | 2014042782 A1 | 3/2014 | | |
| WO | WO-2015051211 A2 * | 4/2015 | ........... | C25B 11/035 |

OTHER PUBLICATIONS

Sen et al., "Electrochemical Reduction of CO2 at Copper Nanofoams," ACS Catalysis (Sep. 5, 2014), vol. 4, No. 9, pp. 3091-3095. ( Year: 2014).*

Popić et al., "Reduction of Carbon Dioxide on Ruthenium Oxide and Modified Ruthenium Oxide Electrodes in 0.5 M NaHCO3," Journal of Electroanalytical Chemistry (Jan. 30, 1997), vol. 421, Nos. 1-2, pp. 105-110. (Year: 1997).*

Glasstone et al., "The Mechanism of the Kolbe Electrosynthesis and Allied Reactions," Seventy-fifth General Meeting, Columbus, OH, Apr. 29, 1939, p. 333, para 2-3; p. 335, para 3; p. 337, para 1; Table 1. abstract.

Sen et al. "Electrochemical Reduction of CO2 at Copper Nanofoams," ACS Catal., 2014, 4 (9), pp. 3091-3095.

International Search Report and Written Opinion issued in corresponding application No. PCT/US2015/053532, dated Feb. 4, 2016, 12 pgs.

Hori, Y. et al., "Electrochemical Reduction of Carbon Dioxide At Various Series of Copper Single Crystal Electrodes," Journal of Molecular Catalysis A: Chemical 199 (2003), pp. 39-47.

Jia, Falong, Xinxing Yu, and Lizhi Zhang. "Enhanced selectivity for the electrochemical reduction of CO2 to alcohols in aqueous solution with nanostructured Cu—Au alloy as catalyst." Journal of Power Sources 252 (2014): 85-89.

Office Action issued for Canadian Application No. 3,000,630, dated Oct. 21, 2021.

Office Action issued for Canadian Application No. 3,000,630, dated May 19, 2022. 3 pages.

* cited by examiner

MATERIALS AND METHODS FOR THE ELECTROCHEMICAL REDUCTION OF CARBON DIOXIDE

CROSS-REFERENCE TO RELATED APPLICATIONS

This application is a continuation of U.S. patent application Ser. No. 16/736,014, filed Jan. 7, 2020, now abandoned, which is a continuation of U.S. patent application Ser. No. 15/516,495, filed Apr. 3, 2017, now abandoned, which is a national stage application filed under 35 U.S.C. § 371 of PCT/US 2015/053532, filed Oct. 1, 2015, which claims benefit of U.S. Provisional Application No. 62/058,121, filed Oct. 1, 2014, each of which are hereby incorporated herein by reference in their entirety.

BACKGROUND

The combustion of fossil fuels in activities such as the electricity generation, transportation, and manufacturing produces billions of tons of carbon dioxide annually. Research since the 1970s indicates increasing concentrations of carbon dioxide in the atmosphere may be responsible for altering the Earth's climate, changing the pH of the ocean and other potentially damaging effects. Countries around the world, including the United States, are seeking ways to mitigate emissions of carbon dioxide.

Converting carbon dioxide into economically valuable materials (e.g., fuels and/or industrial chemicals) offers an attractive strategy for mitigating carbon dioxide emissions. Laboratories around the world have attempted for many years to use electrochemistry and/or photochemistry to convert carbon dioxide to economically valuable products. However, existing methods for the conversion of carbon dioxide suffer from many limitations, including the stability of systems used in the process, the efficiency of systems, the selectivity of the systems or processes for a desired chemical, the cost of materials used in systems/processes, the ability to control the processes effectively, and the rate at which carbon dioxide is converted. No commercially available solutions for converting carbon dioxide to economically valuable fuels or industrial chemicals currently exist.

SUMMARY

Disclosed are methods for electrochemically reducing carbon dioxide to provide one or more products (e.g., fuels and/or industrial chemicals). Methods for electrochemically reducing carbon dioxide to provide a product can comprise contacting the carbon dioxide with an electroreduction catalyst in an electrochemical cell, and applying a potential to the electrochemical cell to form the product. The applied potential can be from −0.10 V to −1.8 V (e.g., from −0.15 V to −1.8 V, or from −0.25 V to −1.6 V) vs. a reversible hydrogen electrode.

The electroreduction catalyst can comprise a nanoporous Cu catalyst; a nanoporous Cu-M catalyst, where M is a metal chosen from Pt, Ir, Pd, Ag, Au, Rh, Ru, Zn, Sn, Ni, Fe, Re, Ga, In, Cd, Tl, and Ti; or a combination thereof. In some embodiments, the electroreduction catalyst be a nanoporous Cu-M catalyst, where M is a metal chosen from Pt, Ir, Pd, Ag, Au, Rh, Ru, Zn, Sn, Ni, Fe, Re, Ga, In, Cd, Tl, and Ti. In some embodiments, the electroreduction catalyst be a nanoporous Cu—Ru catalyst.

In some embodiments, the electroreduction catalyst can comprise nanoparticles having an average particle size of from 10 nm to 500 nm (e.g., from 10 nm to 250 nm, from 10 nm to 150 nm, from 20 nm to 100 nm, from 20 nm to 80 nm, or from 80 nm to 100 nm), as determined by scanning electron microscopy (SEM). The nanoparticles can have a BET surface area of from 5 $m^2/g$ to 40 $m^2/g$ (e.g., from 10 $m^2/g$ to 40 $m^2/g$, from 10 $m^2/g$ to 20 $m^2/g$, or from 20 $m^2/g$ to 40 $m^2/g$).

The electrochemical reduction of carbon dioxide can produce one or more products. The electrochemical reduction of carbon dioxide can be selective towards the formation of $C_2$ and/or $C_3$ species. For example, the one or more products can comprise a $C_2$-$C_3$ alkane, a $C_2$-$C_3$ alkene, a $C_2$-$C_3$ alcohol, a $C_2$-$C_3$ carboxylic acid, a $C_2$-$C_3$ aldehyde, or a combination thereof. In some embodiments, the one or more products can comprise a $C_2$-$C_3$ alkane and/or a $C_2$-$C_3$ alkene (e.g., ethane, ethylene, or a combination thereof). In certain embodiment, the method is selective for the formation of $C_2$-$C_3$ alkanes over methane, such that the $C_2$-$C_3$ alkanes are formed with at least 10 times greater Faradaic efficiency than methane. In some embodiments, the one or more products can comprise a $C_2$-$C_3$ alcohol (e.g., ethanol, propanol, or a combination thereof). In certain embodiments, the one or more products can comprise propanol. In some cases, the propanol can be formed at a Faradaic efficiency of from 0.5% to 15%. In certain embodiment, the method is selective for the formation of $C_2$-$C_3$ alcohols over methanol, such that the $C_2$-$C_3$ alcohols are formed with at least 10 times greater Faradaic efficiency than methanol.

The electrochemical cell can be a divided electrochemical cell that comprises a working electrode comprising the electroreduction catalyst in a first cell compartment, a counter electrode in a second cell compartment, and a solid electrolyte membrane interposed between the working electrode and the counter electrode. Both the first cell compartment and the second cell compartment can further comprise an aqueous solution of an electrolyte. For example, the first cell compartment can further comprise an aqueous solution of an electrolyte in electrochemical contact with the working electrode disposed in the first cell compartment, and the second cell compartment can further comprise an aqueous solution of an electrolyte in electrochemical contact with the counter electrode disposed in the second cell compartment. In these embodiments, contacting the carbon dioxide with the electroreduction catalyst can comprise introducing the carbon dioxide into the first cell compartment of the divided electrochemical cell (e.g., bubbling the carbon dioxide into/through the aqueous solution of the electrolyte). Applying a potential to the electrochemical cell can comprise applying a negative voltage and a positive voltage to the working electrode and die counter electrode, respectively, to reduce the carbon dioxide to form the product. The electrolyte can comprise an alkali metal bicarbonate (e.g., potassium bicarbonate or sodium bicarbonate).

Also provided are systems (e.g., electrochemical cells) and electroreduction catalysts that can be used in conjunction with the methods described herein. For example, provided herein are electrochemical cells that comprise a working electrode comprising an electroreduction catalyst described herein in a first cell compartment; a counter electrode in a second cell compartment; and a solid electrolyte membrane interposed between the working electrode and the counter electrode. Both the first cell compartment and the second cell compartment can further comprise an aqueous solution of an electrolyte. For example, the first cell compartment can further comprise an aqueous solution of an electrolyte in electrochemical contact with the working electrode disposed in the first cell compartment, and the second cell compartment can further comprise an aqueous solution of an electrolyte in electrochemical contact with the counter electrode disposed in the second cell compartment.

DETAILED DESCRIPTION

Figure 1:
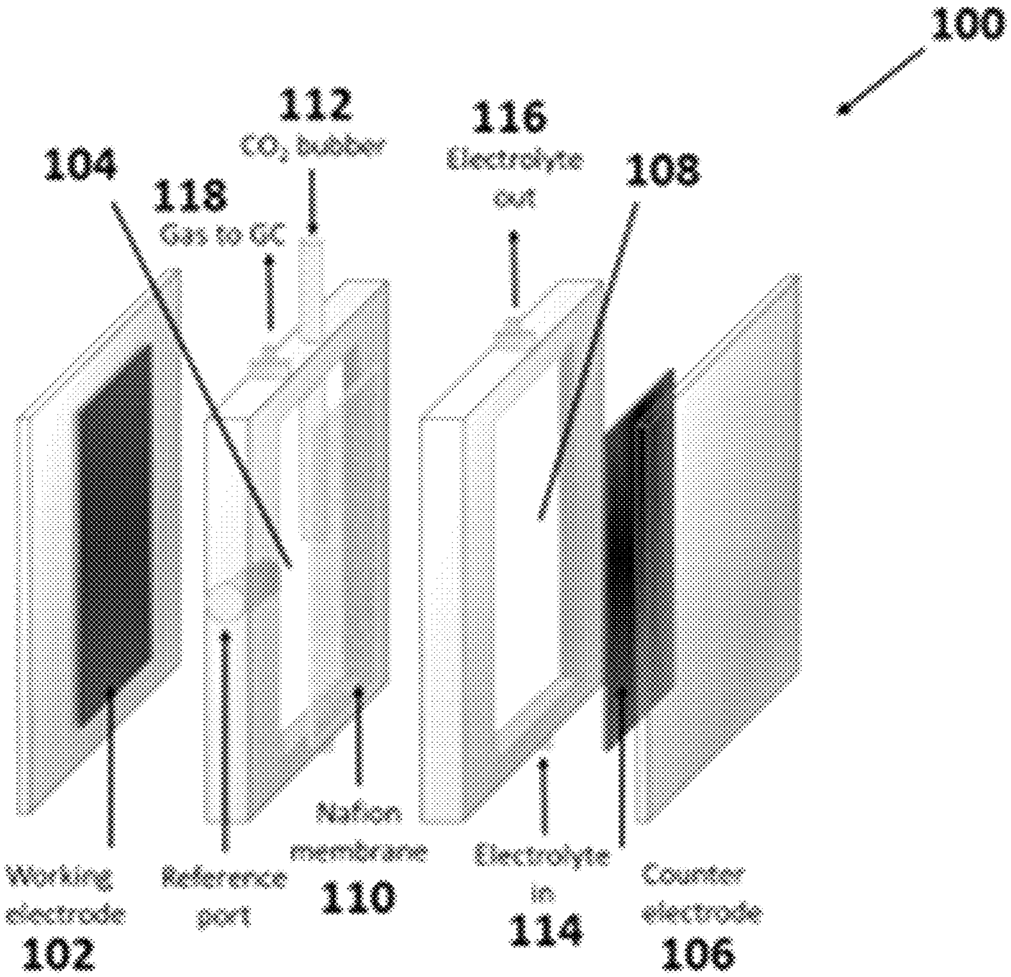
FIG. 1 is an exploded view of an electrochemical cell that can be used in conjunction with the electrochemical reduction of carbon dioxide described herein.
Figure 2:
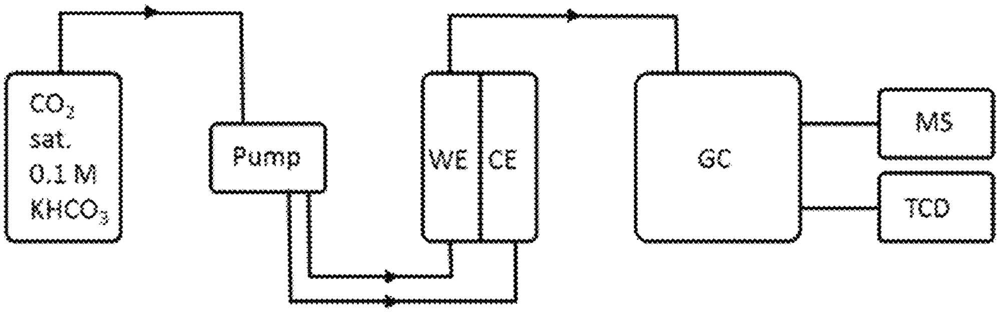
FIG. 2 is a process flow diagram schematically illustrating the methods for the electrochemical reduction of carbon dioxide described herein.

Provided herein are methods for electrochemically reducing carbon dioxide to provide one or more products (e.g., fuels and/or industrial chemicals). Methods for electrochemically reducing carbon dioxide to provide a product can comprise contacting the carbon dioxide with an electroreduction catalyst in an electrochemical cell, and applying a potential to the electrochemical cell to form the product.

The applied potential can be −0.10 V or less (e.g., −0.15 V or less, −0.20 V or less, −0.25 V or less, −0.30 V or less, −0.35 V or less, −0.40 V or less, −0.45 V or less, −0.50 V or less, −0.55 V or less, −0.60 V or less, −0.65 V or less, −0.70 V or less, −0.75 V or less, −0.80 V or less, −0.85 V or less, −0.90 V or less, −0.95 V or less, −1.0 V or less, −1.05 V or less, −1.10 V or less, −1.15 V or less, −1.20 V or less, −1.25 V or less, −1.30 V or less, −1.35 V or less, −1.40 V or less, −1.45 V or less, −1.50 V or less, −1.55 V or less, −1.60 V or less, −1.65 V or less, −1.70 V or less, or −1.75 V or less) vs. a reversible hydrogen electrode. The applied potential can be at least −1.8 V (e.g., at least −1.75 V, at least −1.70 V, at least −1.65 V, at least −1.60 V, at least −1.55 V, at least −1.50 V, at least −1.45 V, at least −1.40 V, at least −1.35 V, at least −1.30 V, at least −1.25 V, at least −1.20 V, at least −1.15 V, at least −1.10 V, at least −1.05 V, at least −1.0 V, at least −0.95 V, at least −0.90 V, at least −0.85 V, at least −0.80 V, at least −0.75 V, at least −0.70 V, at least −0.65 V, at least −0.60 V, at least −0.55 V, at least −0.50 V, at least −0.45 V, at least −0.40 V, at least −0.35 V, at least −0.30 V, at least −0.25 V, at least −0.20 V, or at least −0.15 V) vs. a reversible hydrogen electrode.

The applied potential can range from any of the minimum values described above to any of the maximum values described above. For example, the applied potential can be from −0.10 V to −1.8 V (e.g., from −0.15 V to −1.8 V, from −0.25 V to −1.6 V, from −0.35 V to −1.0 V, or from −1.0 V to −1.6 V) vs. a reversible hydrogen electrode.

The electrochemical reduction of carbon dioxide can produce one or more products. The electrochemical reduction of carbon dioxide can be selective towards the formation of $C_2$ and/or $C_3$ species. Without wishing to be bound by theory, the electroreduction catalysts described herein possess disordered surfaces that include, for example, a large number of grain boundaries that are believed to facilitate carbon-carbon bond formation during the electrochemical reduction of $CO_2$. As a consequence, the catalysts and methods described herein can favor the formation of $C_2$ and/or $C_3$ species.

For example, in some cases, the one or more products can comprise a $C_2$-$C_3$ alkane (e.g., ethane, propane, or a combination thereof), a $C_2$-$C_3$ alkene (e.g., ethylene, propylene, or a combination thereof), a $C_2$-$C_3$ alcohol (e.g., ethanol, propanol, or a combination thereof), a $C_2$-$C_3$ carboxylic acid (e.g., acetic acid, propionic acid, or a combination thereof), a $C_2$-$C_3$ aldehyde (e.g., acetaldehyde, propanal, or a combination thereof), or a combination thereof. The electrochemical reduction of carbon dioxide can also produce other species, such as carbon monoxide, formic acid, or a combination thereof.

In some embodiments, the one or more products can comprise a $C_2$-$C_3$ alkane and/or a $C_2$-$C_3$ alkene (e.g., ethane, ethylene, or a combination thereof). In some examples, the one or more products can comprise ethane, and the ethane can be formed at a Faradaic efficiency of from 0.5% to 15%. In some examples, the one or more products can comprise ethylene, and the ethylene can be formed at a Faradaic efficiency of from 0.5% to 15%. In certain embodiments, the method can be selective for the formation of $C_2$-$C_3$ alkanes over methane, such that the $C_2$-$C_3$ alkanes are formed with at least 10 times greater (e.g., at least 15 times greater, at least 20 times greater, at least 25 times greater, at least 50 times greater, or at least 100 times greater) Faradaic efficiency than methane. In certain examples, methane can be formed at a Faradaic efficiency of less than 0.5% (e.g., less than 0.1%, or less than 0.05%).

In some embodiments, the one or more products can comprise a $C_2$-$C_3$ alcohol (e.g., ethanol, propanol, or a combination thereof). In certain embodiments, the one or more products can comprise propanol. In some cases, the propanol can be formed at a Faradaic efficiency of from 0.5% to 15%. In certain embodiment, the method is selective for the formation of $C_2$-$C_3$ alcohols over methanol, such that the $C_2$-$C_3$ alcohols are formed with at least 10 times greater Faradaic efficiency than methanol. In certain examples, methanol can be formed at a Faradaic efficiency of less than 0.5% (e.g., less than 0.1%, or less than 0.05%).

In some embodiments, the methods for electrochemically reducing carbon dioxide can produce formic acid at relatively high Faradaic efficiencies and low overpotentials. For example, in some examples, formic acid can be formed at a Faradaic efficiency of at least at least 10% (e.g., at least 15%, at least 20%, or at least 25%) at an overpotential of from −0.65 V to −0.95 V (e.g., at an overpotential of −0.65 V, −0.70 V, −0.75 V, −0.80 V, −0.85 V, −0.90 V, or −0.95 V) vs. a reversible hydrogen electrode. In some examples, formic acid can be formed at a Faradaic efficiency of at least at least 5% (e.g., at least 10%, at least 15% or at least 20%) at an overpotential of from −0.25 V to −0.55 V (e.g., at an overpotential of −0.25 V, −0.30 V, −0.35 V, −0.40 V, −0.45 V, −0.50 V, or −0.55 V) vs. a reversible hydrogen electrode.

As discussed above, methods for electrochemically reducing carbon dioxide to provide a product can comprise contacting the carbon dioxide with an electroreduction catalyst. The electroreduction catalyst can comprise a nanoporous Cu catalyst; a nanoporous Cu-M catalyst, where M is a metal chosen from Pt, Ir, Pd, Ag, Au, Rh, Ru, Zn, Sn, Ni, Fe, Re, Ga, In, Cd, Tl, and Ti; or a combination thereof.

The nanoporous Cu catalyst can be a nanoporous, open-cell copper foam. Nanoporous, open-cell copper foams are known in the art, and can be prepared from alloys of copper and a second, less noble metal (e.g., aluminum, zinc, magnesium, tin, etc.). The second, less noble metal can be selectively removed, for example by etching the alloy (a process also referred to as selective leaching or dealloying), to provide a porous copper material. This process can involve contacting an alloy of copper and a second, less noble metal with an etchant for a period of time effective to selectively leach the second, less noble metal from the copper and form a porous copper support. An appropriate etchant can be selected in view of the identity of the second, less noble metal. For example, in some embodiments, the nanoporous, open-cell copper foam can be prepared by etching CuAl alloy (e.g., by contacting the CuAl alloy with a suitable etchant, for example a base such as aqueous sodium hydroxide, for a period of time effective to selectively leach the aluminum from the copper) to form a nanoporous, open-cell copper foam.

The relative amounts of copper and the second, less noble metal in the alloy used to form the nanoporous, open-cell copper foam can be varied in order to influence the properties of the resulting nanoporous, open-cell copper foam (and thus the resulting catalytic properties of the material). In some embodiments, the alloy of copper and a second, less noble metal (e.g., aluminum) can comprise at least 10 atomic percent (at %) copper (e.g., at least 15 at % copper, at least 20 at % copper, at least 25 at % copper, at least 30 at % copper, at least 35 at % copper, at least 40 at % copper, or at least 45 at % copper). In some embodiments, the alloy of copper and a second, less noble metal (e.g., aluminum) can comprise 50 at % or less copper (e.g., 45 at % or less copper, 40 at % or less copper, 35 at % or less copper, 30 at % or less copper, 25 at % or less copper, 20 at % or less copper, or 15 at % or less copper). In some embodiments, the alloy of copper and a second, less noble metal (e.g., aluminum) can comprise at least 50 at % of the second, less noble metal (e.g., at least 55 at % of the second, less noble metal, at least 60 at % of the second, less noble metal, at least 65 at % of the second, less noble metal, at least 70 at % of the second, less noble metal, at least 75 at % of the second, less noble metal, at least 80 at % of the second, less noble metal, or at least 85 at % of the second, less noble metal). In some embodiments, the alloy of copper and a second, less noble metal (e.g., aluminum) can comprise 90 at % or less of the second, less noble metal (e.g., 85 at % or less of the second, less noble metal, 80 at % or less of the second, less noble metal, 75 at % or less of the second, less noble metal, 70 at % or less of the second, less noble metal, 65 at % or less of the second, less noble metal, 60 at % or less of the second, less noble metal, or 55 at % or less of the second, less noble metal).

The relative amounts of copper and the second, less noble metal (e.g., aluminum) in the alloy (e.g., CuAl) used to form the nanoporous, open-cell copper foam can range from any of the minimum values described above to any of the maximum values described above. For example, the alloy of copper and a second, less noble metal (e.g., aluminum) can comprise from 10 to 50 at % copper and from 50 to 90 at % of the second, less noble metal (e.g., Al). In certain embodiments, the alloy used to form the nanoporous, open-cell copper foam can be a CuAl alloy that comprises from 10 to 50 at % copper and from 50 to 90 at % aluminum (e.g., from 10 to 30 at % copper and from 70 to 90 at % aluminum).

The nanoporous Cu-M catalyst can be a nanoporous, open-cell Cu-M alloy foam. Nanoporous, open-cell Cu-M alloy foams can be prepared by galvanically depositing a metal M (e.g., Pt, Ir, Pd, Ag, Au, Rh, Ru, Zn, Sn, Ni, Fe, Re, Ga, In, Cd, Tl, and Ti) on a nanoporous, open-cell copper foam to form the nanoporous, open-cell Cu-M alloy foam. Methods for producing the nanoporous Cu-M catalyst can comprise galvanically depositing a catalytically effective amount of a desired metal (M) on a nanoporous, open-cell copper foam (e.g., at a temperature greater than 5° C.) to form a Cu-M precursor catalyst; and conditioning the Cu-M precursor catalyst to form the nanoporous Cu-M catalyst.

Galvanic deposition can involve contacting the nanoporous, open-cell copper foam with a solution (e.g., an aqueous solution) comprising an M-containing species (e.g., a Pt, Ir, Pd, Ag, Au, Rh, Ru, Zn, Sn, Ni, Fe, Re, Ga, In, Cd, Tl, or Ti-containing species). The M-containing species can comprise a suitable metal complex that can participate in a spontaneous galvanic-reaction with the copper in the nanoporous, open-cell copper foam. By way of example, in the case of the galvanic deposition of Pt, the Pt-containing species can comprise a platinum metal complex that can participate in a spontaneous galvanic-reaction with the copper in the porous copper support, such as $PtCl_4^{2-}$, $PtCl_6^{2-}$, or combinations thereof.

In some embodiments, the nanoporous, open-cell copper foam can be disposed on a surface (e.g., the surface of an electrode) in contact with the solution comprising the M-containing species during galvanic deposition. In certain embodiments, the surface comprising the nanoporous, open-cell copper foam can be rotated during galvanic deposition. The surface can be rotated at a rate effective to induce a laminar flow of the solution comprising the M-containing species towards and across the surface on which the nanoporous, open-cell copper foam is disposed during galvanic deposition. This can drive uniform deposition of the metal on the nanoporous, open-cell copper foam. In certain embodiments, the surface can be rotated at a rate of from 250 rpm to 2000 rpm (e.g., from 250 rpm to 1500 rpm, or from 250 rpm to 750 rpm).

The galvanic deposition can be performed at varying temperatures to provide nanoporous Cu-M catalysts having the desired properties for a particular catalytic application. In some embodiments, the galvanic deposition can be performed at a temperature greater than 5° C. (e.g., at least 10° C., at least 15° C., at least 20° C., at least 25° C., at least 30° C., at least 35° C., at least 40° C., at least 45° C., at least 50° C., at least 55° C., at least 60° C. at least 65° C. at least 70° C., at least 75° C., at least 80° C., at least 85° C., at least 90° C., at least 95° C., at least 100° C., at least 110° C. at least 120° C., at least 130° C., at least 140° C., at least 150° C., at least 160° C., at least 170° C. at least 180° C., or at least 190° C.). In some embodiments, the galvanic deposition can be performed at a temperature of 200° C. or less (e.g., 190° C. or less, 180° C. or less, 170° C. or less, 160° C. or less, 150° C. or less, 140° C. or less, 130° C. or less, 120° C. or less, 110° C. or less, 100° C. or less, 95° C. or less, 90° C. or less, 85° C. or less, 80° C. or less, 75° C. or less, 70° C. or less, 65° C. or less, 60° C. or less, 55° C. or less, 50° C. or less, 45° C. or less, 40° C. or less, 35° C. or less, 30° C. or less, 25° C. or less, 20° C. or less, 15° C. or less, or 10° C. or less).

The galvanic deposition can be performed at a temperature ranging from any of the minimum temperature values described above to any of the maximum temperatures described above. For example, in some embodiments, the metal is galvanically deposited at a temperature of from 5° C. to 200° C. (e.g., from 5° C. to 170° C., from 5° C. to 150° C., from 5° C. to 120° C., from 5° C. to 90° C., from 5° C. to 90° C., from 25° C. to 90° C., from 5° C. to 60° C., or from 25° C. to 60° C.).

The galvanic deposition can be performed for varying periods of time, so as to provide nanoporous Cu-M catalysts having a molar ratio of Cu:M desired for use in a particular catalytic application. For example, the nanoporous, open-cell copper foam can be maintained is maintained in contact with the solution comprising the M-containing species for a period of time effective to form a nanoporous Cu-M catalyst having desired a molar ratio of Cu:M.

The molar ratio of Cu:M in the nanoporous Cu-M catalyst can be determined by Inductively Coupled Plasma-Mass Spectroscopy (ICP-MS). In some embodiments, molar ratio of Cu:M in the nanoporous Cu-M catalyst can be at least 1:2 (e.g., at least 1:1, at least 1.25:1, at least 1.5:1, at least 1.6:1, at least 1.7:1, at least 1.8:1, at least 1.9:1, at least 2:1, at least 2.1:1, at least 2.2:1, at least 2.3:1, at least 2.4:1, at least 2.5:1, at least 5:1, at least 10:1, at least 25:1, at least 50:1, at least 100:1, at least 150:1, at least 200:1, or at least 250:1). In some embodiments, molar ratio of Cu:M in the nanoporous Cu-M catalyst can be 500:1 or less (e.g., 250:1 or less, 200:1 or less, 150:1 or less, 100:1 or less, 50:1 or less, 25:1 or less, 10:1 or less, 5:1 or less, 2.5:1 or less, 2.4:1 or less, 2.3:1 or less, 2.2:1 or less, 2.1:1 or less 2:1 or less, 1.9:1 or less, 1.8:1 or less, 1.7:1 or less, 1.6:1 or less, 1.5:1 or less, 1.25:1 or less, or 1:1 or less).

The molar ratio of Cu:M in the nanoporous Cu-M catalyst can range from any of the minimum ratios described above to any of the maximum ratios described above. For example, the molar ratio of Cu:M in the nanoporous Cu-M catalyst, as determined by ICP-MS, can range from 1:2 to 500:1 (e.g., from 1:2 to 250:1; from 1:1 to 500:1; from 1:1 to 250:1; from 5:1 to 500:1; from 10:1 to 500:1; from 0.5:1 to 2.5:1, from 1:1 to 2.5:1, or from 1.5:1 to 2.2:1).

Following galvanic deposition, the Cu-M precursor catalyst can be conditioned to form the nanoporous Cu-M catalyst. Conditioning can involve electrochemical dealloying of the Cu-M precursor catalyst to form the nanoporous Cu-M catalyst. For example, the Cu-M precursor catalyst can be conditioned by repeated electrochemical cycling (e.g., 50 cycles) of the Cu-M precursor catalyst between 0.5 V and 1.2 V at 25° C. in $N_2$-saturated 0.1 M $HClO_4$ to dealloy/stabilize the catalyst.

In some embodiments, the electroreduction catalyst (e.g., the nanoporous Cu catalyst; the nanoporous Cu-M catalyst, where M is a metal chosen from Pt, Ir, Pd, Ag, Au, Rh, Ru. Zn. Sn, Ni, Fe, Re. Ga, In, Cd, Tl, and Ti; or a combination thereof) can be processed to reduce the particle size of the electroreduction catalyst prior to use in conjunction with the methods described herein. For example, in some embodiments, the electroreduction catalyst can be formed into nanoparticles prior to use in conjunction with the methods described herein.

The electroreduction catalyst can be formed into nanoparticles prior to use in conjunction with the methods described herein using any suitable method known in the art. The nanoparticles formed by the process can be spherical or non-spherical in shape. In certain embodiments, the nanoparticles can be discrete, spherical nanoparticles. In some embodiments, the population of nanoparticles formed by this process is monodisperse. The nanoparticles can optionally comprise nanopores. In some embodiments, the nanopores can interconnect, so as to form a network of nanopores spanning the nanoparticles.

"Monodisperse" and "homogeneous size distribution," as used herein, and generally describe a population of particles where all of the particles are the same or nearly the same size. As used herein, a monodisperse distribution refers to particle distributions in which 80% of the distribution (e.g., 85% of the distribution, 90% of the distribution, or 95% of the distribution) lies within 25% of the median particle size (e.g., within 20% of the median particle size, within 15% of the median particle size, within 10% of the median particle size, or within 5% of the median particle size).

"Mean particle size" or "average particle size", are used interchangeably herein, and generally refer to the statistical mean particle size of the particles in a population of nanoparticles. The diameter of an essentially spherical particle can refer to the physical diameter of the spherical particle. The diameter of a non-spherical nanoparticle can refer to the largest linear distance between two points on the surface of the nanoparticle. Mean particle size can be measured using methods known in the art, such as evaluation by scanning electron microscopy.

In some embodiments, the electroreduction catalyst can comprise nanoparticles having an average particle size, as measured by scanning electron microscopy (SEM), of at least 10 nm (e.g., at least 15 nm, at least 20 nm, at least 25 nm, at least 30 nm, at least 35 nm, at least 40 nm, at least 45 nm, at least 50 nm, at least 55 nm, at least 60 nm, at least 65 nm, at least 70 nm, at least 75 nm, at least 80 nm, at least 85 nm, at least 90 nm, at least 95 nm, at least 100 nm, at least 150 nm, at least 200 nm, at least 250 nm, at least 300 nm, at least 350 nm, at least 400 nm, or at least 450 nm). In some embodiments, the electroreduction catalyst can comprise nanoparticles having an average particle size, as measured by SEM, of 500 nm or less (e.g., 450 nm or less, 400 nm or less, 350 nm or less, 300 nm or less, 250 nm or less, 200 nm or less, 150 nm or less, 100 nm or less, 95 nm or less, 90 nm or less, 85 nm or less, 80 nm or less, 75 nm or less, 70 nm or less, 65 nm or less, 60 nm or less, 55 nm or less, 50 nm or less, 45 nm or less, 40 nm or less, 35 nm or less, 30 nm or less, 25 nm or less, 20 nm or less, or 15 nm or less).

The electroreduction catalyst can comprise nanoparticles having an average particle size, as measured by SEM, ranging from any of the minimum values described above to any of the maximum values described above. For example, the electroreduction catalyst can comprise nanoparticles having an average particle size, as measured by SEM, of from 10 nm to 500 nm (e.g., from 10 nm to 250 nm, from 10 nm to 150 nm, from 20 nm to 100 nm, from 20 nm to 80 nm, or from 80 nm to 100 nm, from 10 nm to 80 nm, from 25 nm to 80 nm, or from 50 nm to 80 nm).

In some embodiments, the electroreduction catalyst can have a specific surface area of at least 5 $m^2/g$, as measured using the Brunauer-Emmett-Teller (BET) method (e.g, at least 10 $m^2/g$, at least 15 $m^2/g$, at least 20 $m^2/g$, at least 25

$m^2/g$, at least 30 m g, or at least 35 $m^2/g$). In some embodiments, the electroreduction catalyst can have a specific surface area of 40 $m^2/g$ or less, as measured using the BET method (e.g, 35 $m^2/g$ or less, 30 $m^2/g$ or less, 25 $m^2/g$ or less, 20 $m^2/g$ or less, 15 $m^2/g$ or less, or 10 $m^2/g$ or less).

The electroreduction catalyst can have a specific surface area ranging from any of the minimum values described above to any of the maximum values described above. For example, the electroreduction catalyst can have a specific surface area of from 5 $m^2/g$ to 40 $m^2/g$, as measured using the BET method (e.g., from 10 $m^2/g$ to 40 $m^2/g$, from 10 $m^2/g$ to 25 $m^2/g$, from 10 $m^2/g$ to 20 $m^2/g$, from 20 $m^2/g$ to 40 $m^2/g$, or from 10 $m^2/g$ to 15 $m^2/g$).

The electroreduction catalysts can be disposed on a conductive substrate (e.g., the surface of an electrode, such as a copper electrode (e.g., copper foil) or carbon electrode) to form an electrode for use in conjunction with the methods described herein.

For some applications, including many catalytic applications, it may be of interest to deposit the electroreduction catalysts described herein on a support, such as a carbonaceous support. Accordingly, also provided are compositions comprising a electroreduction catalyst described herein deposited on a support, such as a carbonaceous support. The carbonaceous support may comprise any type of carbon that suitably supports the electroreduction catalyst to provide a catalyst having suitable activity. The carbonaceous support can comprise an amorphous carbon, a crystalline or graphitic carbon, or a vitreous or glassy carbon. Also, the carbonaceous support can be in any suitable form (e.g., in the form of a powder, fiber, or flake), and can have any suitable crystallographic orientation, crystallite size, interlayer spacing, density, particle size, or particle shape. The carbonaceous support can comprise a carbon selected from Ketjen Black, carbon black, lamp black, acetylene black, mesocarbon, graphite, pyrolytic graphite, single-wall carbon nanotubes, multi-wall carbon nanotubes, Vulcan carbon, and carbon fiber. In some embodiments, the carbonaceous support can have an average particle size of from 0.01 μm to 10 μm. The supported electroreduction catalysts can also be disposed on a conductive substrate to provide an electrode.

The electrochemical cell can be, for example, a divided electrochemical cell. An exploded view of an example electrochemical cell that can be used in conjunction with the electrochemical reduction of carbon dioxide described herein is illustrated in FIG. 1. As shown in FIG. 1, the electrochemical cell (100) can comprise a working electrode (102) comprising the electroreduction catalyst in electrochemical contact with a first cell compartment (104) and a counter electrode (106) in electrochemical contact with a second cell compartment (108). A solid electrolyte membrane (110) (e.g., a cation exchange membrane such as a Nafion® membrane) can be interposed between the working electrode (102) and the counter electrode (106).

Both the first cell compartment and the second cell compartment can further comprise an aqueous solution of an electrolyte. For example, the first cell compartment can further comprise an aqueous solution of an electrolyte in electrochemical contact with the working electrode disposed in the first cell compartment, and the second cell compartment can further comprise an aqueous solution of an electrolyte in electrochemical contact with the counter electrode disposed in the second cell compartment. Any suitable electrolyte can be used. For example, the electrolyte can be selected to as to be compatible with carbon dioxide present in the system (e.g., so as not to precipitate upon introduction of carbon dioxide into the electrochemical cell). For example, the electrolyte can comprise potassium bicarbonate, sodium hydrogen carbonate, potassium chloride, potassium sulfate, or potassium phosphate. In certain embodiments, the electrolyte can comprise an alkali metal bicarbonate (e.g., potassium bicarbonate or sodium bicarbonate).

The electrochemical cell can further comprise a gas inlet (112) that can be used to introduce carbon dioxide into the first cell compartment of the divided electrochemical cell. The cell can further include other features to facilitate operation, including an electrolyte inlet (114) and an electrolyte outlet (116) fluidly connected to the second cell compartment that can be used to introduce electrolyte into the electrochemical cell, and a product outlet (118) that can be used to remove products from the first cell compartment. If desired, the electrochemical cell can further include a reference electrode configured to measure the potential when the electrochemical cell is used for electrocatalysis.

In these embodiments when electrochemical cells of this design are utilized, contacting the carbon dioxide with the electroreduction catalyst can comprise introducing the carbon dioxide into the first cell compartment of the divided electrochemical cell (e.g., bubbling the carbon dioxide into/through the aqueous solution of the electrolyte). Applying a potential to the electrochemical cell can comprise applying a negative voltage and a positive voltage to the working electrode and the counter electrode, respectively, to reduce the carbon dioxide to form the product. The reaction can be performed at room temperature (i.e., 23° C.) and standard pressure of $CO_2$ (1 bar). Methods can further include obtaining one or more products of the reduction reaction from the first cell compartment and/or (in the case of multiple products) separating one or more products to obtain a desired product from the reduction reaction.

The electroreduction catalysts described herein can also be used in other catalytic applications. For example, the electroreduction catalysts can also be used as an electrocatalyst for the electrolytic coupling of carboxylic acids (i.e. the Kolbe reaction). For example, provided herein are methods for preparing an organic compound defined by Formula II from a carboxylic acid defined by Formula I and a carboxylic acid defined by Formula I' according to the equation below $$\underset{\text{Formula I}}{RCOOH} + \underset{\text{Formula I'}}{R'COOH} + 1/2\ O_2 \longrightarrow \underset{\text{Formula II}}{R\text{—}R'} + CO_2 + H_2O$$

where R and R' interdependently represent hydrogen, a substituted or unsubstituted alkyl group (e.g., a substituted or unsubstituted $C_1$-$C_{12}$ alkyl group), a substituted or unsubstituted alkenyl group (e.g., a substituted or unsubstituted $C_2$-$C_{12}$ alkenyl group), a substituted or unsubstituted alkynyl group (e.g., a substituted or unsubstituted $C_2$-$C_{12}$ alkynyl group), a substituted or unsubstituted aryl group (e.g., a substituted or unsubstituted phenyl group), a substituted or unsubstituted heteroaryl group (e.g., a substituted or unsubstituted $C_3$-$C_{10}$ heteroaryl group), a substituted or unsubstituted alkylaryl group, or a substituted or unsubstituted alkylheteroaryl group. The method can comprise contacting the carboxylic acid defined by Formula I and the carboxylic acid defined by Formula I' with an electroreduction catalyst described herein in an electrochemical cell, and applying a potential to the electrochemical cell to form the organic compound defined by Formula II.

The examples below are intended to further illustrate certain aspects of the methods, systems, and compositions described herein, and are not intended to limit the scope of the claims.

EXAMPLES

Materials and Methods

Sodium hydroxide pellets (Certified ACS, 97%), methanol (Certified ACS, 99.8%), phosphoric acid (85% in water), and potassium bicarbonate (USP/FCC grade) were purchased from Fisher Scientific. Copper foil (99.98%, 0.5 mm thick) and Nafion® membrane (NRE-212) were purchased from Sigma Aldrich. Nafion® solution (5% w/w) was purchased from Alfa Aesar. Ruthenium trichloride hydrate (>99%) was purchased from Pressure Chemical Co. Hydrogen, carbon dioxide, and helium (all 99.995%) were purchased from Praxair. Copper/aluminum rods were made in-house, using a composition of 83 at % aluminum. The potassium bicarbonate electrolyte solution was pre-electrolyzed and filtered before use, using deionized water for dilution (MilliQ, Advantage A10).

Preparation of Nanoporous Copper Foams

A CuAl rod of known percent composition was mechanically cut into smaller coins. The CuAl coins were placed into 6 M NaOH, which was heated to 80° C. and stirred for 24 hours to etch out the Al, forming nanoporous Cu foams.

Figure 3:
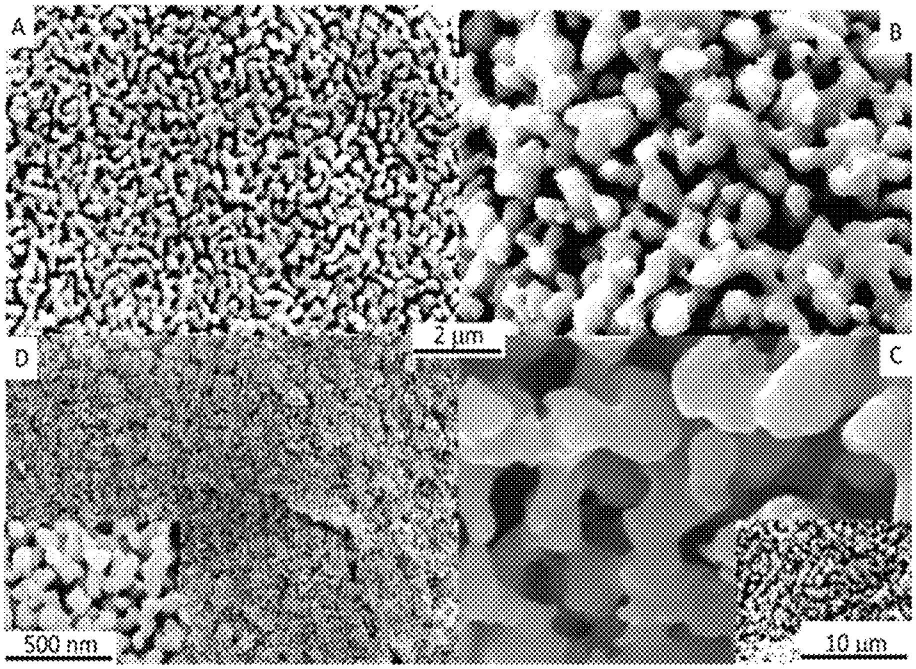
FIG. 3 shows scanning electron microscopy (SEM) images of nanoporous, open cell copper foams prepared using four different etching regimes: panel A (top left) 30 at % CuAl alloy etched in 6 M NaOH, at 80° C. and 10 mA/g; panel B (top right) 30 at % CuAl alloy etched in 6 M NaOH, at 80° C. and 0 mA/g; panel C (bottom right) 30 at % CuAl alloy etched in 6 M NaOH, at 80° C. and 100 mA/g; and panel D (bottom left) 17 at % CuAl alloy etched in 6 M NaOH, at 80° C. and 0 mA/g.
Figure 4:
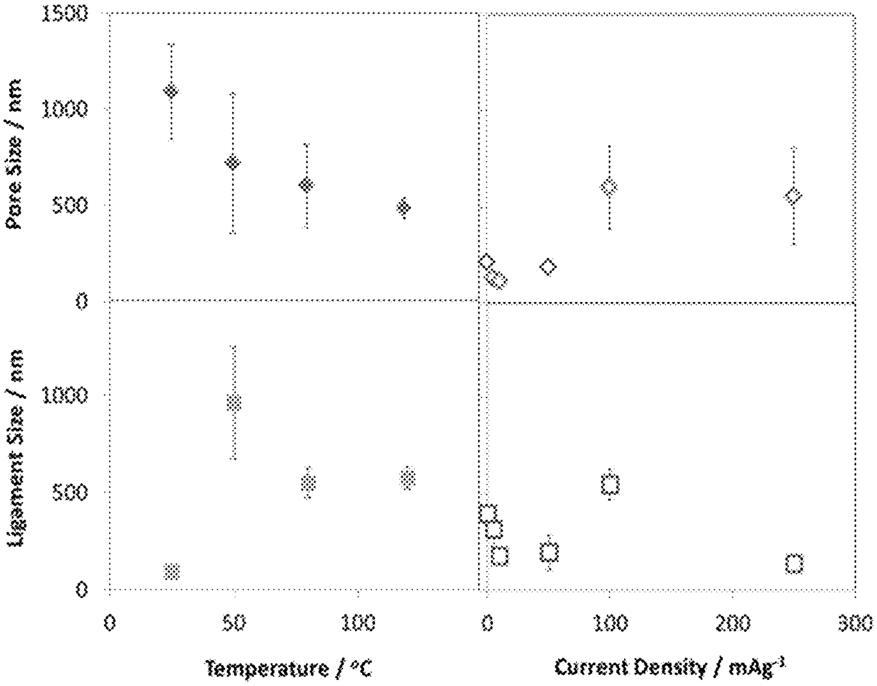
FIG. 4 is a plot illustrating the effect of the etching temperature (° C.) and etching current (mA/g) on the pore size (nm) and ligament size (nm) of nanoporous, open cell copper foams.

If desired, the porosity of the nanoporous Cu foams can be further tuned with temperature (e.g., by varying the heating temperature from 0° C. to 100° C.), strength of the NaOH etchant (e.g., by varying the concentration of the NaOH etchant from 0.1 to 6 M), etching current (e.g., by varying the etching current from 0 to 300 mA/g), or a combination thereof. FIG. 3 includes SEM images of nanoporous Cu foams prepared at various conditions. By varying process conditions, nanoporous Cu foams possessing tunable pores and correspondingly a range of materials with tunable surface area can be obtained. BET surface area analysis shows that the surface area of the nanoporous Cu foams can be tuned between 5 $m^2/g$ and 40 $m^2/g$.

The nanoporous copper foams were then soaked in DI water for 12 hours and rinsed repeatedly. The foams were then dried in an oven at 60° C. for 1 hour. The foams were then reduced under $H_2$ atmosphere in a tube furnace (Lindberg Blue M, Thermo Scientific) at 400° C. for 2 hours. The nanoporous copper foams were then stored in a vacuum sealed container until use.

Preparation of Nanoporous Copper Coating Solution

A nanoporous copper foam was crushed. 0.015 g of the crushed nanoporous copper foam was then mixed with 10 mL of methanol in a glass cylinder, the mixture was degassed for 1 minute; the mixture was then sonicated for 10 minutes (FS30D, Fisher Scientific). 40 μL of Nafion® solution was added, and the mixture was sonicated for an additional 10 minutes.

Preparation of Nanoporous Copper Electrode.

Copper foils were cut to an appropriate size and electropolished in 85% phosphoric acid at 1.4 V vs a platinum wire counter electrode for 10 minutes. The foils were then rinsed in DI water and dried under $N_2$. The foil was then placed into a custom built aluminum box and the nanoporous copper coating solution was cast onto the foil. The solution was then placed in an oven at 60° C. for approximately 1 hour, or until dry. The nanoporous copper foil was then reduced under $H_2$ on a hot plate in the following order: 200° C. (20 min.) →100° C. (10 min.)→RT (5 min.). A water layer was applied until the foil was placed into an electrochemical flow cell.

Preparation of Nanoporous Copper/Ruthenium Electrodes

Copper foils were cut to an appropriate size and electropolished in 85% phosphoric acid at 1.4 V vs a platinum wire counter electrode for 10 minutes. The foils were then rinsed in DI water and dried under $N_2$. The foil was then placed into a custom built aluminum box and the nanoporous copper coating solution was cast onto the foil. The solution was then placed in an oven at 60° C. for approximately 1 hour, or until dry. Approximately 0.100 g of ruthenium chloride monohydrate was mixed with 300 mL of DI water. The mixture was heated to 100° C. and stirred, then purged using $N_2$ gas for 30 minutes. The nanoporous copper coated foil was submerged into the ruthenium solution for 1 hour and galvanic displacement of ruthenium for copper occurred. The nanoporous copper/ruthenium foil was then reduced under $H_2$ on a hot plate in the following order: 200° C. (20 min.) →100° C. (10 min.)→RT (5 min.). A water layer was applied until the foil was placed into an electrochemical flow cell.

$CO_2$ Electroreduction

Electroreduction experiments were performed at ambient temperature and pressure in a custom two-compartment electrochemical cell (FIG. 1). The cell was sealed using Viton® gaskets. The counter electrode was a dimensionally stabilized anode. The electrolyte was 0.1 M $KHCO_3$ saturated with $CO_2$. The pH of the saturated solution was 6.8. The working and counter compartments were separated using a Nafion® cation exchange membrane. An RHE reference electrode was used for all experiments. The RHE was created by flowing $H_2$ over a piece of black Pt gauze in the 0.1 M $KHCO_3$ electrolyte. The pH of the solution at the RHE was 9.2. A volume of 26 mL of electrolyte in the working compartment was held static throughout the experiment and continuously saturated with $CO_2$ at a flow rate of approximately 10 mL/min. Headspace gas was vented directly to the gas chromatograph (7890A, Agilent Technologies) through a sampling loop. The combined $CO_2$ and product gas flow rate was measured at the end of the sampling loop by a soap bubble flow meter (Model 520, Fisher Scientific). Electrolyte in the counter compartment was continuously replenished to maintain ionic conductivity of the solution

Product Analysis

Potentiostatic experiments were performed for 65 minutes per data point (Model 253A, Princeton Applied Research). Injections were made into the gas chromatograph every 13 minutes. The gas chromatograph had two columns to which the product gases were split to: a Haysep Q column equipped with a mass spectrometer, and a Molesieve 5A column equipped with a thermal conductivity detector. The mass spectrometer was used to quantify $C_2H_4$ and $C_2H_6$ concentration and the thermal conductivity detector was used to quantify $H_2$ and CO concentration.

The liquid electrolyte in the working compartment of the electrolysis cell was collected at the end of the experiment and analyzed using an AVIII 400 MHz NMR spectrometer. NMR samples were prepared by mixing 0.8 mL of the collected electrolyte with 0.1 mL $D_2O$ and 0.1 mL of 100 ppm acetonitrile as an internal standard. A water suppression method was used to measure the $^1H$ spectrum. This allowed for identification and quantification of formate, acetone, ethanol, and propanol.

Figure 5:
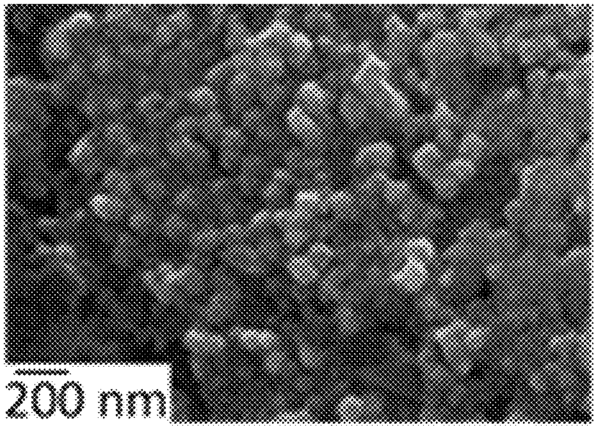
FIG. 5 shows an SEM image of a nanoporous CuRu catalyst.

Ex situ experiments were performed to observe the nanostructured material and determine the amount of ruthenium present after galvanic displacement. Samples used in ex situ experiments were reduced under $H_2$ and heat in the manner described above Results and Discussion Characterization of Catalysts and Electrodes FIG. 5 is an SEM image of nanoporous CuRu catalyst for use in $CO_2$ reduction. The SEM shows relatively uniform distribution of CuRu nanoparticles in the range of 80-100 nm.

Figure 6:
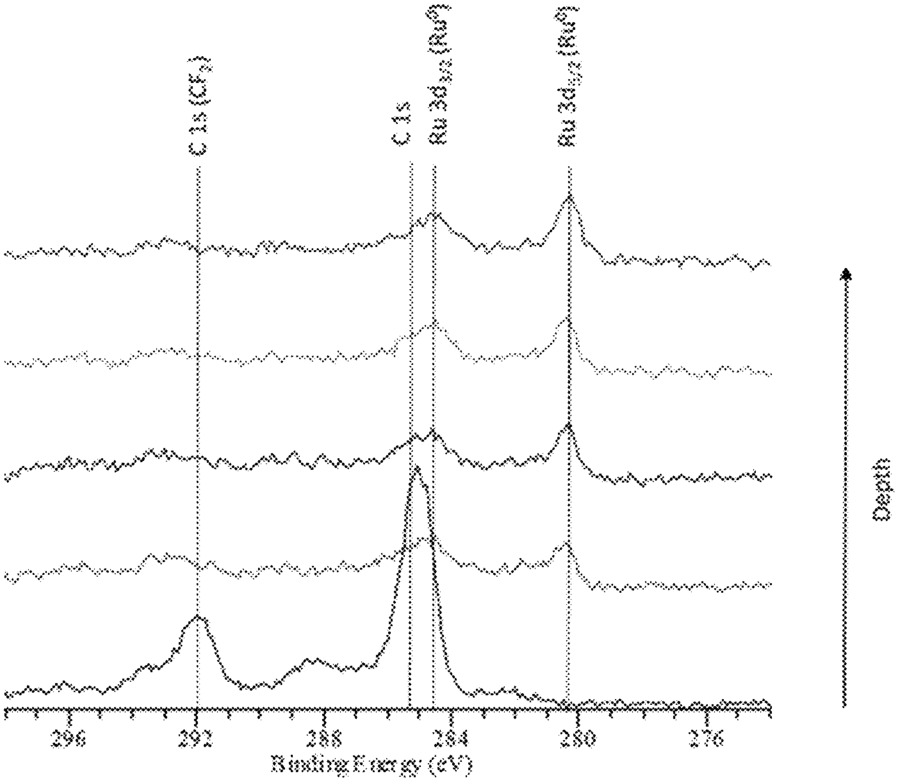
FIG. 6 shows an overlay plot of x-ray photoelectron spectroscopy (XPS) spectra of a post-electrolysis CuRu electrode at varying depths. XPS spectra of the surface indicate a lack of ruthenium present on the surface. Repeated $Ar^+$ etching reveals the presence of ruthenium metal within a few atomic layers below the surface.

X-ray photoelectron spectroscopy (XPS) was used to characterize the nanoporous copper/ruthenium electrode. XPS spectra were obtained on a Kratos XPS using monochromatic Al Kα radiation. Spectra were obtained from both the surface and several atomic layers below the surface of newly made and used electrodes. See FIG. 6.

The copper 2p peaks clearly show the presence of a copper oxide layer, which should be expected, as these samples were handled briefly in air before being transported to XPS for analysis. The Cu LMM peaks show a strong signal at 917.5 eV (KE), correlating strongly with Cu (II). It is possible that both Cu (I) and Cu (II) are present. Etching the surface using $Ar^+$ ion-bombardment resulted in a complete removal of the oxide layer.

Ruthenium 3d peaks are found at a similar binding energy as adventitious carbon. Newly made CuRu samples are shown to have $RuO_2$ present on the surface while ruthenium metal is found just below the surface, after an $Ar^+$ etch. CuRu that has been used for $CO_2$ reduction shows metallic Ru several atomic layers below the surface while Ru is not detected on the top most surface layer. The data suggests that Ru migrated from the surface to the bulk of the sample and was thereafter evenly dispersed throughout the material.

Electrocatalytic $CO_2$ Activity and Selectivity

Figure 7:
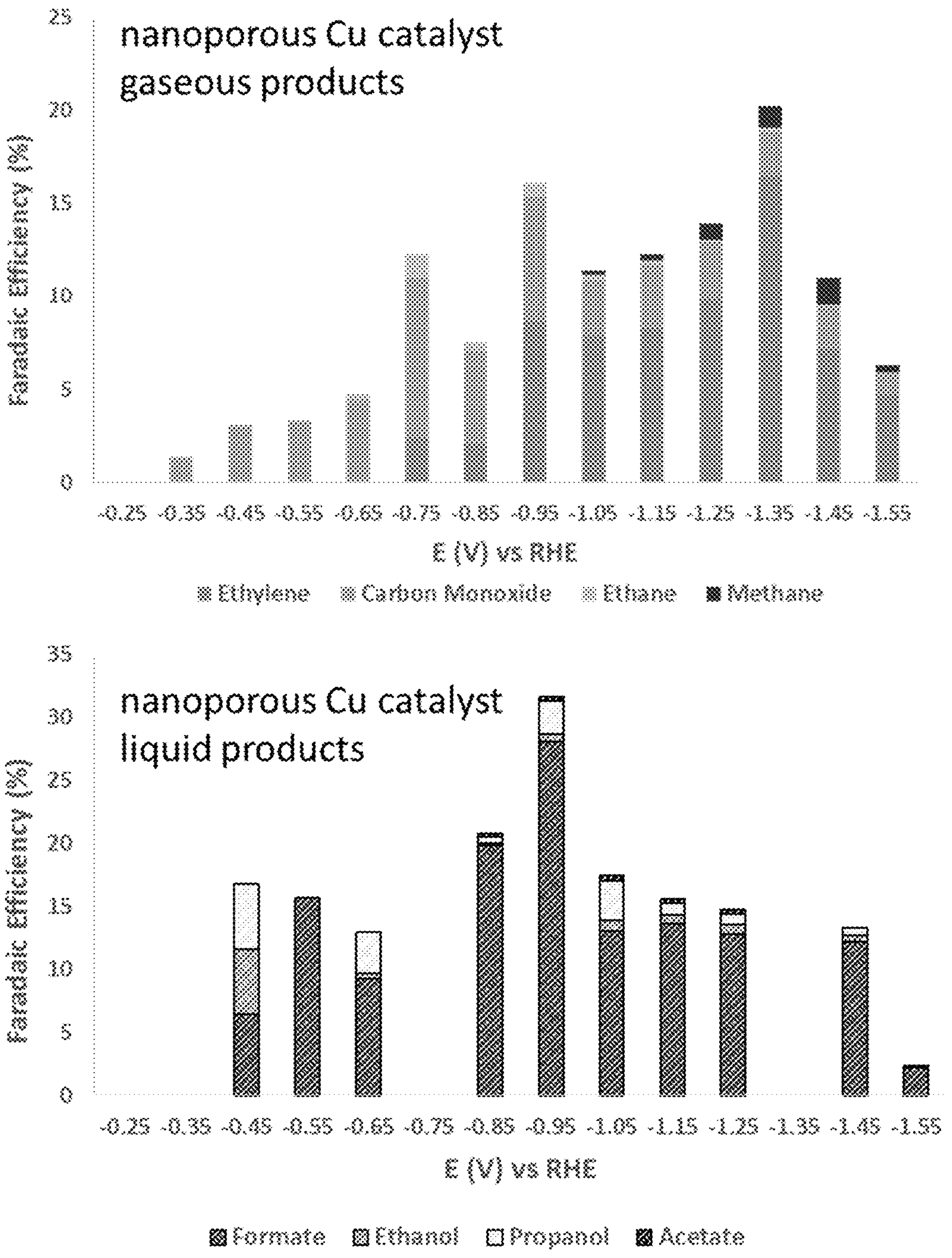
FIG. 7 is a plot of the Faradaic efficiencies for gaseous $CO_2$ reduction products (top) and liquid $CO_2$ reduction products (bottom) as a function of applied potential (versus the reversible hydrogen electrode) obtained using a nanoporous Cu catalyst.
Figure 8:
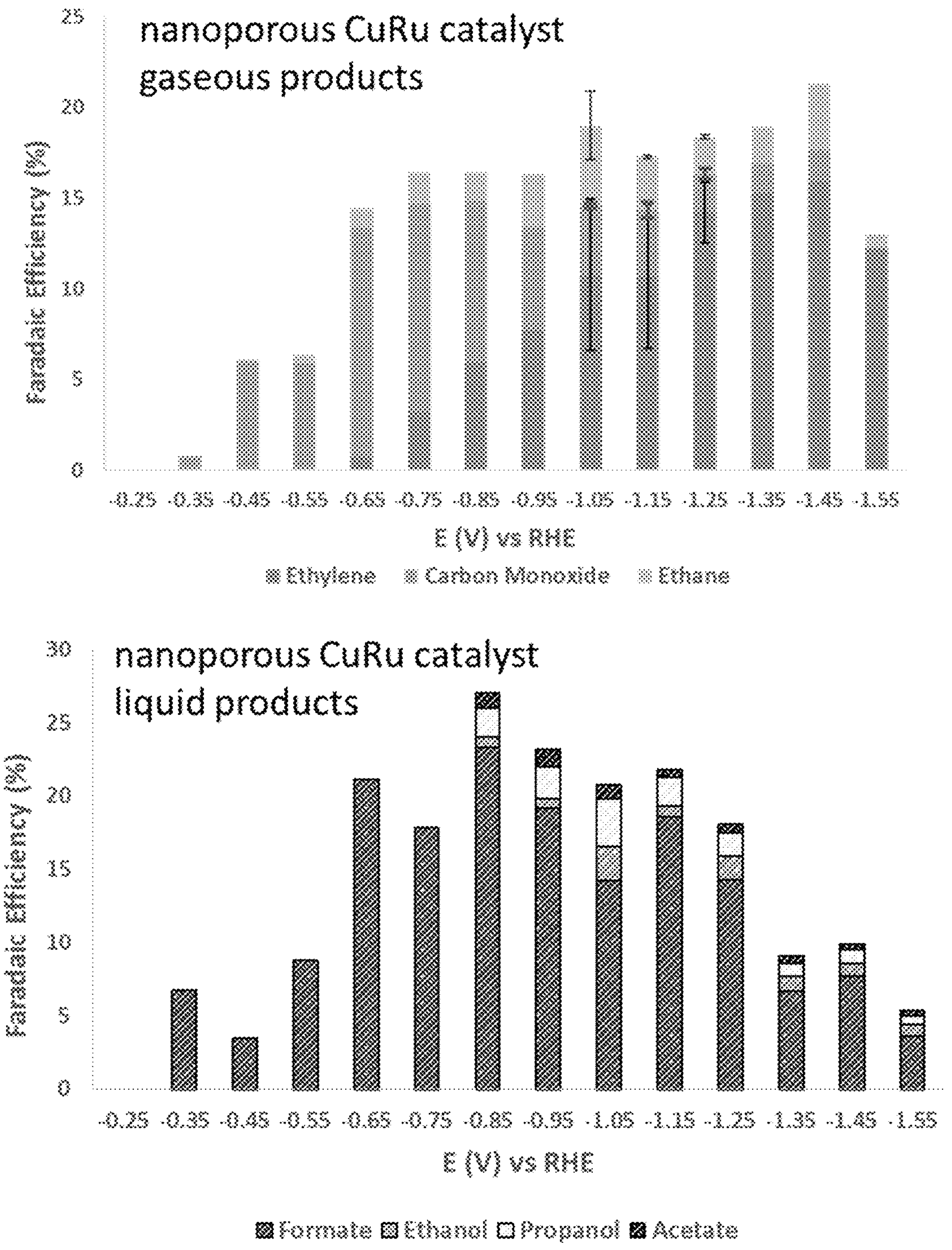
FIG. 8 is a plot of the Faradaic efficiencies for gaseous $CO_2$ reduction products (top) and liquid $CO_2$ reduction products (bottom) as a function of applied potential (versus the reversible hydrogen electrode) obtained using a nanoporous Cu—Ru catalyst.

Electroreduction of carbon dioxide on the nanoporous Cu and nanoporous CuRu catalyst resulted in the product distribution shown in FIGS. 7 and 8 for the gas and liquid products respectively. The electrochemical activity of both nanoporous Cu and nanoporous CuRu catalysts is typically around 10 mA/cm$^2$. The onset of $CO_2$ reduction was not observed until an applied potential of −0.35 V. At this potential, carbon monoxide and formate were the only $CO_2$ reduction products from both nanoporous Cu and nanoporous CuRu catalyst. A lower onset potential implies lower power requirement for the electrosynthesis process to occur. Generally, more hydrocarbon products are produced on the nanoporous CuRu catalyst compared to nanoporous Cu. On nanoporous CuRu, CO reached a maximum efficiency of 13% at −0.65 V while the formation of formate reached 30% at −0.95 V on nanoporous Cu. Ethane is consistently produced on the nanoporous CuRu catalysts with an onset at −0.55 V. Significant amounts of ethylene is produced >15%, at −0.65 V, which is almost 100 mV less overpotential required than typically observed on copper foil surfaces. Ethane is another compound that is not typically formed on Cu catalyst. The conversion of $CO_2$ directly to ethane has only been detected on Fe, Co, and Ni catalysts at high pressures of 50 to 60 atmospheres and large overpotential of −1.65 V. A significant amount of ethane (~5%) was detected at early as −0.55 V, an over 1100 mV advantage over existing catalysts. On nanoporous CuRu, no methane or methanol was observed at any of the applied potentials. Ethanol and propanol were detected in the liquid phase with propanol reaching a maximum efficiency of 6.5%. The onset potential of −0.85 V, one of the lowest onset potential reported for propanol formation.

The devices, systems, and methods of the appended claims are not limited in scope by the specific devices, systems, and methods described herein, which are intended as illustrations of a few aspects of the claims. Any devices, systems, and methods that are functionally equivalent are intended to fall within the scope of the claims. Various modifications of the devices, systems, and methods in addition to those shown and described herein are intended to fall within the scope of the appended claims. Further, while only certain representative devices, systems, and method steps disclosed herein are specifically described, other combinations of the devices, systems, and method steps also are intended to fall within the scope of the appended claims, even if not specifically recited. Thus, a combination of steps, elements, components, or constituents may be explicitly mentioned herein or less, however, other combinations of steps, elements, components, and constituents are included, even though not explicitly stated.

The term "comprising" and variations thereof as used herein is used synonymously with the term "including" and variations thereof and are open, non-limiting terms. Although the terms "comprising" and "including" have been used herein to describe various embodiments, the terms "consisting essentially of" and "consisting of" can be used in place of "comprising" and "including" to provide for more specific embodiments of the invention and are also disclosed Other than where noted, all numbers expressing geometries, dimensions, and so forth used in the specification and claims are to be understood at the very least, and not as an attempt to limit the application of the doctrine of equivalents to the scope of the claims, to be construed in light of the number of significant digits and ordinary rounding approaches.

Unless defined otherwise, all technical and scientific terms used herein have the same meanings as commonly understood by one of skill in the art to which the disclosed invention belongs. Publications cited herein and the materials for which they are cited are specifically incorporated by reference.

What is claimed is:

1. A method for electrochemically reducing carbon dioxide to provide a product, the method comprising contacting the carbon dioxide with an electroreduction catalyst in an electrochemical cell, and applying a potential to the electrochemical cell to form the product, wherein the electroreduction catalyst comprises a nanoporous Cu—Ru catalyst;

wherein the product comprises $C_2$-$C_3$ alkanes, $C_2$-$C_3$ alkenes, $C_2$-$C_3$ alcohols, $C_2$-$C_3$ carboxylic acids, $C_2$-$C_3$ aldehydes, or a combination thereof; and wherein the electroreduction catalyst is prepared by a method that comprises galvanically depositing ruthenium on a nanoporous copper foam to form a precursor catalyst; and conditioning the precursor catalyst.

2. The method of claim 1, wherein the electroreduction catalyst comprises nanoparticles having an average particle size of from 10 nm to 500 nm, as determined by scanning electron microscopy (SEM).

3. The method of claim 2, wherein the nanoparticles have a BET surface area of from 10 m$^2$/g to 40 m$^2$/g.

4. The method of claim 1, wherein the product comprises ethanol, propanol, or a combination thereof.

5. The method of claim 4, wherein the product comprises propanol.

6. The method of claim 5, wherein the propanol is formed at a Faradaic efficiency of from 0.5% to 15%.

7. The method of claim 1, wherein the method is selective for the formation of $C_2$-$C_3$ alcohols over methanol, such that the $C_2$-$C_3$ alcohols are formed with at least 10 times greater Faradaic efficiency than methanol.

8. The method of claim 1, wherein the product comprises ethane, ethylene, or a combination thereof.

9. The method of claim 1, wherein the method is selective for the formation of the $C_2$-$C_3$ alkanes over methane, such that the $C_2$-$C_3$ alkanes are formed with at least 10 times greater Faradaic efficiency than methane.

10. The method of claim 1, wherein the electrochemical cell is a divided electrochemical cell comprising:

a working electrode comprising the electroreduction catalyst in a first cell compartment, a counter electrode in a second cell compartment, and a solid electrolyte membrane interposed between the working electrode and the counter electrode, both the first cell compartment and the second cell compartment further comprising an aqueous solution of an electrolyte;

wherein contacting the carbon dioxide with the electroreduction catalyst comprises introducing the carbon dioxide into the first cell compartment of the divided electrochemical cell; and wherein applying a potential to the electrochemical cell comprises applying a negative voltage and a positive voltage to the working electrode and the counter electrode, respectively, to reduce the carbon dioxide to form the product.

11. The method of claim 10, wherein the electrolyte comprises an alkali metal bicarbonate.

12. The method of claim 11, wherein the alkali metal bicarbonate is potassium bicarbonate.

13. The method of claim 1, wherein the applied potential is from −0.15 V to −1.8 V vs. a reversible hydrogen electrode.

14. The method of claim 1, wherein the electroreduction catalyst comprises nanoparticles having an average particle size of from 80 nm to 100 nm, as determined by scanning electron microscopy (SEM).

15. The method of claim 1, wherein the electroreduction catalyst is prepared by a method that further comprises processing the precursor catalyst to reduce a particle size of the precursor catalyst.

16. The method of claim 1, wherein galvanically depositing the ruthenium on within the nanoporous copper foam comprises contacting the nanoporous copper foam with a solution comprising a ruthenium-containing species at a temperature of from 5° C. to 200° C.

17. The method of claim 1, wherein the nanoporous Cu—Ru catalyst comprises Cu and Ru in a molar ratio of Cu:Ru of from 1:2 to 500:1.

18. The method of claim 1, wherein the applied potential is from −0.15 V to −1.8 V vs. a reversible hydrogen electrode; and wherein the method is selective for the formation of the $C_2$-$C_3$ alkanes over methane and the $C_2$-$C_3$ alkanes are produced with at least 10 times greater Faradaic efficiency than methane.

* * * * *